(12) United States Patent
Hoodless et al.

(10) Patent No.: US 9,820,809 B2
(45) Date of Patent: Nov. 21, 2017

(54) ELECTROSURGICAL INSTRUMENT

(71) Applicant: GYRUS MEDICAL LIMITED, Cardiff (GB)

(72) Inventors: Richard John Hoodless, South Gloucestershire (GB); Richard John Keogh, Caerphilly (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 409 days.

(21) Appl. No.: 14/313,156

(22) Filed: Jun. 24, 2014

(65) Prior Publication Data

US 2014/0378969 A1 Dec. 25, 2014

(30) Foreign Application Priority Data

Jun. 24, 2013 (GB) .................................. 1311197.6

(51) Int. Cl.
*A61B 18/14* (2006.01)
*B23P 17/00* (2006.01)
*A61B 18/16* (2006.01)
*A61B 17/00* (2006.01)

(52) U.S. Cl.
CPC ...... *A61B 18/1492* (2013.01); *A61B 18/1485* (2013.01); *B23P 17/00* (2013.01);
(Continued)

(58) Field of Classification Search
CPC ................ A61B 18/14; A61B 18/1402; A61B 2018/1417; A61B 18/148; A61B 18/1482;
(Continued)

(56) References Cited

U.S. PATENT DOCUMENTS 4,742,818 A * 5/1988 Hughes .............. G02B 23/2453
600/133
4,848,339 A 7/1989 Rink et al.
(Continued)

FOREIGN PATENT DOCUMENTS

EP 0 962 191 12/1999
GB 2 477 351 8/2011

OTHER PUBLICATIONS

Communication and Extended European Search Report/communication corresponding to Patent Application No. 14172238.9; dated Dec. 10, 2014.
(Continued)

*Primary Examiner* — Jaymi Della
(74) *Attorney, Agent, or Firm* — Nixon & Vanderhye PC

(57) ABSTRACT

An electrosurgical instrument is provided for the treatment of tissue, the instrument (3) including a shaft (14) and a tip portion including at least one electrode (16), located at the distal end of the shaft. A fluid impermeable sheath (25) covers at least a proportion of the shaft and extends to the tip portion where it terminates in a distal end portion (26). A metallic shroud (29) is provided, comprising an annular ring portion (30) and a rearwardly extending cylindrical portion (31). The ring portion (30) is connected to the tip portion, and the cylindrical portion (31) overlies the distal end portion (26) of the sheath (25) so as to prevent ingress of fluids at the distal end portion of the sheath.

14 Claims, 2 Drawing Sheets

(52) U.S. Cl.
CPC .............. *A61B 2017/00526* (2013.01); *A61B 2018/1467* (2013.01); *A61B 2018/1472* (2013.01); *A61B 2018/162* (2013.01); *Y10T 29/49117* (2015.01)

(58) Field of Classification Search
CPC ............ A61B 18/1485; A61B 18/1487; A61B 18/1492; A61B 2018/1467; A61B 2018/126; A61B 2018/00005; A61B 2018/00011; A61B 2018/00029; A61B 2018/162; A61B 2218/002
See application file for complete search history.

(56) References Cited

U.S. PATENT DOCUMENTS

| | | |
|---|---|---|
| 5,211,625 A | 5/1993 | Sakurai et al. |
| 5,372,138 A | 12/1994 | Crowley et al. |
| 2004/0193150 A1* | 9/2004 | Sharkey ............ A61B 18/1402 606/41 |
| 2005/0234446 A1* | 10/2005 | Van Wyk ........... A61B 18/1485 606/41 |
| 2007/0100337 A1 | 5/2007 | Kawahara et al. |
| 2008/0045943 A1* | 2/2008 | Wittkampf ......... A61B 18/1492 606/41 |
| 2008/0091193 A1* | 4/2008 | Kauphusman ..... A61B 18/1492 606/41 |
| 2009/0138009 A1* | 5/2009 | Viswanathan ..... A61B 18/1492 606/41 |
| 2010/0057072 A1 | 3/2010 | Roman et al. |
| 2011/0196364 A1* | 8/2011 | Morris .............. A61B 18/1402 606/33 |
| 2012/0004685 A1 | 1/2012 | Kienzle et al. |

OTHER PUBLICATIONS

Search Report for GB 1311197.6 dated Dec. 17, 2013.

* cited by examiner

ELECTROSURGICAL INSTRUMENT

CROSS REFERENCE TO RELATED APPLICATION

This application claims priority from and incorporates herein by reference UK Patent Application No. GB 1311197.6, filed Jun. 24, 2013.

TECHNICAL FIELD

This invention relates to an electrosurgical instrument for the treatment of tissue. Such systems are commonly used for the vaporisation and/or coagulation of tissue in surgical intervention, most commonly in "keyhole" or minimally invasive surgery, but also in "open" surgery.

BACKGROUND TO THE INVENTION AND PRIOR ART

One type of electrosurgical procedure is known as "underwater" electrosurgery, in which the instrument is operated submerged in an electrically conductive fluid such as normal saline. Even in dry field electrosurgery, the surgical site is often wet, either due to the presence of blood or irrigating fluid. There is often therefore a requirement for the electrosurgical instrument to be sealed such that fluid does not penetrate the instrument and reach the internal components. Fluid ingress can cause unwanted arcing between components, and for this reason electrosurgical instruments are frequently covered with a fluid impermeable sheath. However, even with such a sheath, unwanted fluid ingress can still occur.

SUMMARY OF THE INVENTION

In order to address the above, embodiments of the invention provide an electrosurgical instrument with improved resistance to fluid ingress. Accordingly, from one aspect an electrosurgical instrument is provided for the treatment of tissue, the instrument including a) a shaft having a longitudinal axis defining a proximal and a distal direction, b) a tip portion located at the distal end of the shaft, the tip portion including at least one electrode, c) a fluid impermeable sheath covering at least a proportion of the shaft and extending to the tip portion where it terminates in a distal end portion, and d) a metallic shroud comprising an annular ring portion and a rearwardly extending cylindrical portion, the arrangement being that the ring portion is connected to the tip portion, and the cylindrical portion overlies the distal end portion of the sheath so as to prevent ingress of fluids at the distal end portion of the sheath.

The metallic shroud covers the distal end of the fluid impermeable sheath and prevents fluid from encroaching at the point where the sheath meets the tip portion of the instrument. Conveniently, the ring portion of the metallic shroud is connected to the tip portion at a location distal of the point where the sheath terminates in a distal end portion. In this way, the rearwardly extending cylindrical portion overlies the point where the sheath terminates, so as to shield it from fluid ingress.

The ring portion is preferably connected to the tip portion by a process involving heating the ring portion, typically by being welded to the tip portion. Conveniently, the ring portion is laser welded to the tip portion. Preferably, the heat process is such that the fluid impermeable sheath is melted in the region of the cylindrical portion of the metallic shroud so as to be sealed against the cylindrical portion. In this way, not only does the shroud cover the distal end portion of the sheath, but also melts the sheath such that it is sealed up against the shroud. By melting the sheath in the region of the cylindrical portion, the barrier against fluid ingress is improved.

Typically, the tip portion includes a bipolar electrode assembly comprising at least one active electrode and at least one return electrode. In this construction, the ring portion is preferably connected to the return electrode. This means that the metallic shroud is electrically connected to the return electrode, and forms an extension of the return electrode in order to conduct current flowing from the active electrode.

The electrosurgical instrument is conveniently an endoscopic surgical instrument. Such instruments are typically used in arthroscopic, laparoscopic or gynaecological surgery, together with an endoscope or other visualisation instrument in a minimally invasive process.

Embodiments of the invention also reside in a method of manufacturing an electrosurgical instrument comprising:

a) providing a shaft, a tip portion including at least one electrode, a fluid impermeable sheath, and a metallic shroud comprising an annular ring portion and a rearwardly extending cylindrical portion, b) securing the tip portion at the distal end of the shaft, c) applying the fluid impermeable sheath to the shaft such that it covers at least a proportion of the shaft and extends to the tip portion where it terminates in a distal end portion, d) applying the metallic shroud such that the cylindrical portion covers the distal end portion of the sheath, and e) welding the annular ring portion to the tip portion such that it is secured thereto, in such a way that the heat from the welding process also heats the cylindrical portion and melts the fluid impermeable sheath in the location thereof, sealing it to the cylindrical portion.

BRIEF DESCRIPTION OF THE DRAWINGS

Embodiments of the invention will now be further described, by way of example only, with reference to the accompanying drawings, in which.

DESCRIPTION OF THE EMBODIMENTS

Figure 1:
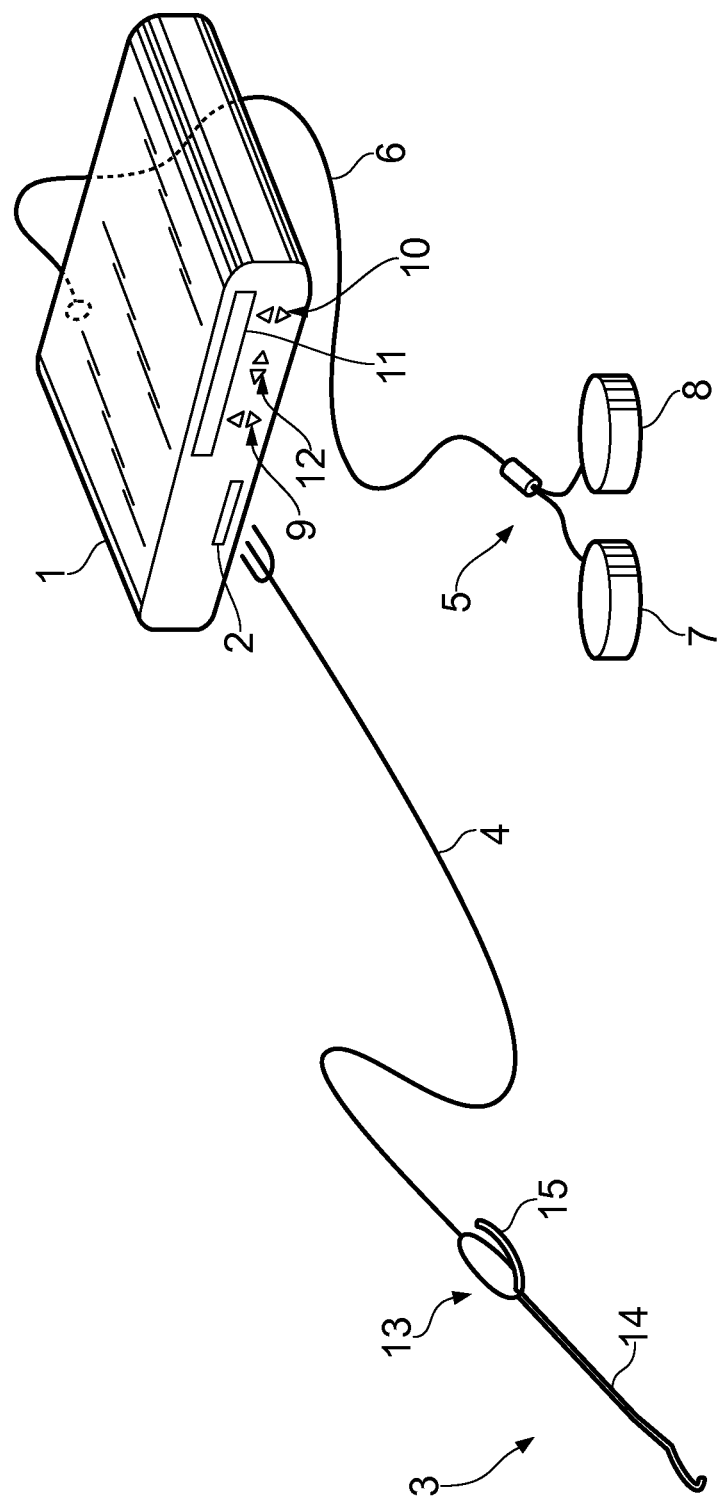
FIG. 1 is a schematic diagram of an electrosurgical system using an electrosurgical instrument in accordance with an embodiment of the present invention.

Referring to the drawings, FIG. 1 shows electrosurgical apparatus including a generator 1 having an output socket 2 providing a radio frequency (RF) output, via a connection cord 4, for an electrosurgical instrument 3. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a desiccation mode and a vaporisation mode of the generator 1 respectively. The generator front panel has push buttons 9 and 10 for respectively setting desiccation and vaporisation power levels, which are indicated in a display 11. Push buttons 12 are provided as an alternative means for selection between the desiccation and vaporisation modes.

The electrosurgical instrument 3 comprises a housing 13 with an elongate shaft 14, and tissue treatment electrodes at the distal end of the shaft, as will be described below. A movable handle 15 associated with the housing can be actuated to cause the shaft to bend. This instrument is particularly suited to the treatment of the hip joint, where a relatively long shaft with articulation capability is needed to access the area to the treated.

Figure 2:
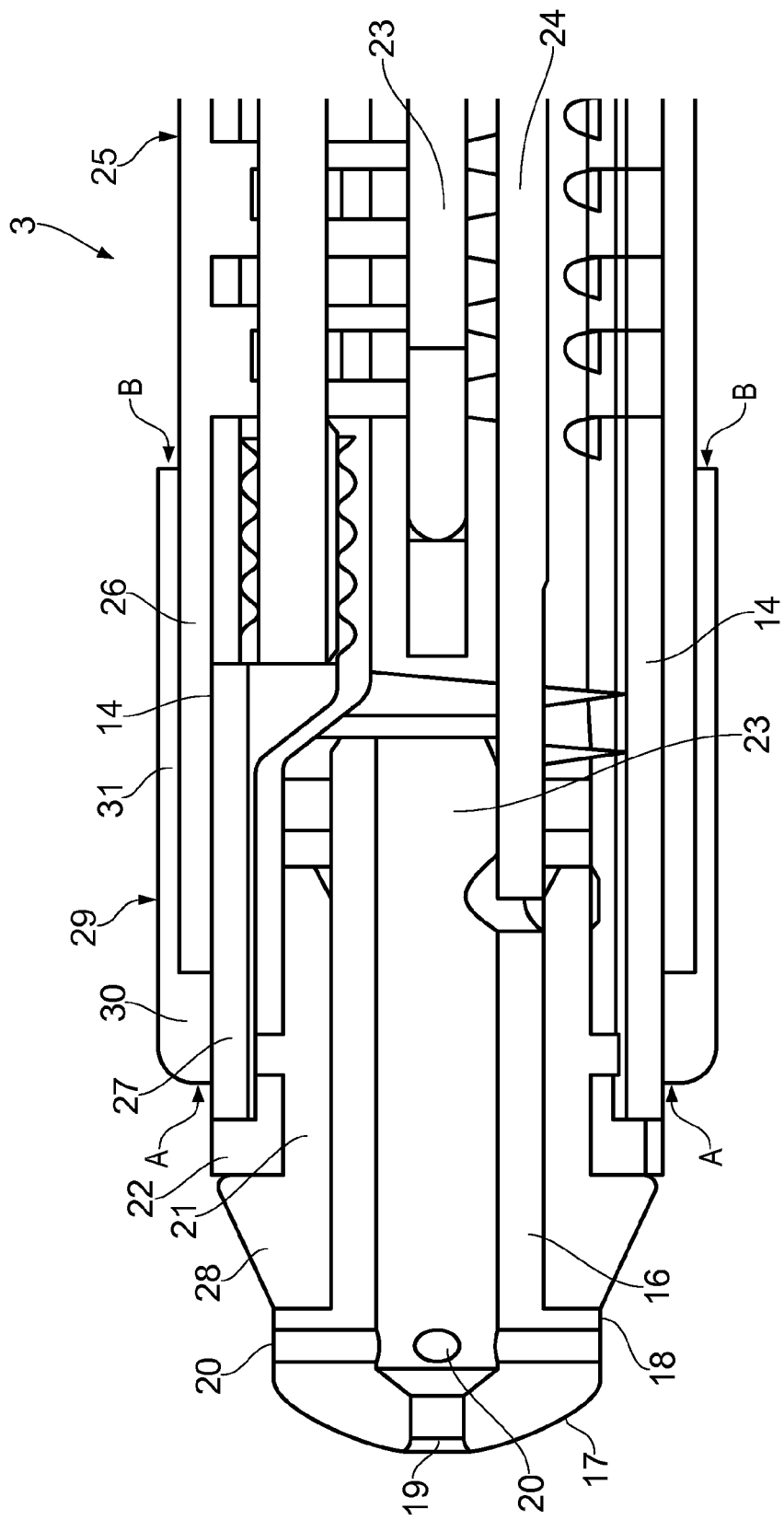
FIG. 2 is a cross-sectional side view of the tip of an electrosurgical instrument in accordance with the embodiment of the present invention.

FIG. 2 shows the tip of the electrosurgical instrument 3, and includes an active tissue treatment electrode 16 comprising a hemispherical end face 17 and a cylindrical side face 18. The electrode is typically formed from tungsten (or an alloy of tungsten and platinum), and can be formed from a single integral component or from two components welded one to the other. The end face 17 is provided with a single aperture 19 located at the centre thereof, while the side face 18 is provided with a plurality of apertures 20 spaced at equal distances around its circumference. The tissue treatment electrode is located on a ceramic component 21, and held in place by a split ring retainer 22 which is laser welded in place. The electrode 16 and ceramic component 21 are both hollow so as to form a suction lumen 23, and also to accommodate a lead 24 to supply RF energy to the tissue treatment electrode 16.

The majority of the shaft 14 is covered by a fluid impermeable insulating sheath 25, the insulating sheath having and end portion 26 leaving a portion of the shaft uncovered in order to form a return electrode 27. The return electrode 27 is separated from the tissue treatment electrode 16 by a portion of the ceramic component, forming an insulator 28. A metallic shroud 29 is located over the end of the sheath 25, the shroud comprising an annular ring portion 30 and a rearwardly extending cylindrical portion 31. The ring portion 30 is laser welded to the exposed part of the shaft 14, at that part forming the return electrode 27. The cylindrical portion 31 overlies the end portion 26 of the sheath, and the heat from the laser welding of the ring portion 30 causes the sheath material to melt and form a seal against the cylindrical portion 31.

In use the instrument 3 is introduced into the body of a patient and manoeuvred into position, typically adjacent a hip joint. RF energy is supplied to the tissue treatment electrode 16, which is used to vaporise or coagulate tissue depending on the type of RF energy supplied from the generator 1. The instrument is typically used submerged in an electrically conductive fluid, such as normal saline, with the RF energy flowing from the tissue treatment electrode 16, through the conductive liquid to the return electrode 27, with any tissue entering the region of the tissue treatment electrode 16 being vaporised or coagulated depending on the circumstances.

Saline ingress into the interior of the instrument 3 is prevented at point A by the laser welding of the annular ring portion 30 to the shaft 14. Similarly, saline ingress is prevented at point B by the sealing of the end portion 26 of the sheath 25 to the cylindrical portion 31 of the shroud 29. The only points at which saline can flow into the interior of the instrument is through the apertures 19 & 20, which lead to the sealed suction lumen 23 which controls the saline flow. In this way, saline does not penetrate the other areas of the instrument, and unwanted arcing is therefore prevented.

Alternative embodiments will be envisaged by those skilled in the art without departing from the scope of the present invention. For example, the electrosurgical instrument can also be used as a monopolar instrument, with just the electrode 16 being connected to the generator 1 together with a remote patient return pad (not shown). Whichever type of instrument is employed, the shroud 29 helps to prevent saline ingress to the interior of the instrument, avoiding unwanted heating of components and arcing therebetween.

The invention claimed is:

1. An electrosurgical instrument, including:
   a) a shaft having a longitudinal axis defining a proximal and a distal direction,
   b) a tip portion located at a distal end of the shaft, the tip portion including at least one active tissue treatment electrode,
   c) a fluid impermeable sheath covering at least a portion of an outside of the shaft and extending to the tip portion where it terminates in a distal end portion, the fluid impermeable sheath forming an external fluid impermeable boundary over the portion of the outside of the shaft covered by the fluid impermeable sheath, and
   d) a metallic shroud comprising an annular ring portion and a rearwardly extending cylindrical portion, the annular ring portion being connected to the tip portion, and the rearwardly extending cylindrical portion overlying the distal end portion of the fluid impermeable sheath so as to prevent ingress of fluids at the distal end portion of the fluid impermeable sheath, a cross-sectional thickness of the annular ring portion being greater than a cross-sectional thickness of the rearwardly extending cylindrical portion, thereby allowing clearance for the distal end portion of the fluid impermeable sheath to be received under the rearwardly extending cylindrical portion of the metallic shroud so that the rearwardly extending cylindrical portion overlies the distal end portion so as to prevent the ingress of the fluids at the distal end portion.

2. The electrosurgical instrument according to claim 1, wherein the annular ring portion is connected to the tip portion at a location distal of a point where the fluid impermeable sheath terminates in a distal end portion.

3. The electrosurgical instrument according to claim 1, wherein the annular ring portion is connected to the tip portion by a process involving heating the ring portion.

4. The electrosurgical instrument according to claim 3, wherein the annular ring portion is welded to the tip portion.

5. The electrosurgical instrument according to claim 4, wherein the annular ring portion is laser welded to the tip portion.

6. The electrosurgical instrument according to claim 3, wherein the fluid impermeable sheath is melted in a region of the rearwardly extending cylindrical portion of the metallic shroud so as to be sealed against the rearwardly extending cylindrical portion.

7. The electrosurgical instrument according to claim 1, wherein the tip portion includes a bipolar electrode assembly comprising the at least one active tissue treatment electrode and at least one return electrode.

8. The electrosurgical instrument according to claim 7, wherein the annular ring portion is connected to the return electrode.

9. The electrosurgical instrument according to claim 1, wherein the electrosurgical instrument is an endoscopic surgical instrument.

10. The electrosurgical instrument according to claim 1, wherein the at least one active tissue treatment electrode comprising a hemispherical end face and a cylindrical side face.

11. The electrosurgical instrument according to claim 10, wherein the hemispherical end face is provided with a single aperture located at a center of the hemispherical end face, and wherein the cylindrical side face is provided with a plurality of apertures spaced at equal distances around a circumference of the cylindrical side face.

12. The electrosurgical instrument according to claim 10, wherein the at least one active tissue treatment electrode is located on a ceramic component and held in place by a split ring retainer which is laser welded in place.

13. The electrosurgical instrument according to claim 12, wherein the at least one active tissue treatment electrode and the ceramic component are both hollow so as to form a suction lumen, and also to accommodate a lead for supplying radio frequency (RF) energy to the at least one active tissue treatment electrode.

14. A method of manufacturing the electrosurgical instrument according to claim 1, the method comprising the steps of:

a) providing the shaft, the tip portion including the at least one active tissue treatment electrode, the fluid impermeable sheath, and the metallic shroud comprising the annular ring portion and the rearwardly extending cylindrical portion,
b) securing the tip portion at the distal end of the shaft,
c) applying the fluid impermeable sheath to the shaft such that it covers at least a proportion of the shaft and extends to the tip portion where it terminates in a distal end portion,
d) applying the metallic shroud such that the cylindrical portion covers the distal end portion of the sheath, and
e) welding the annular ring portion to the tip portion such that it is secured thereto, in such a way that heat from the welding process also heats the cylindrical portion and melts the fluid impermeable sheath in the location thereof, sealing the fluid impermeable sheath to the cylindrical portion.

\* \* \* \* \*